United States Patent [19]
Ohwaki et al.

[11] Patent Number: 5,462,869
[45] Date of Patent: Oct. 31, 1995

[54] HUMAN ENDOTHELIN CONVERTING ENZYME ISOLATED FROM BLOOD OR PLACENTA BY HYDRATED DENSITY

[75] Inventors: Tatsuya Ohwaki, Ohimachi; Hiroshi Sakai, Ohi, both of Japan

[73] Assignee: Nisshin Flour Milling Co., Ltd., Tokyo, Japan

[21] Appl. No.: 247,413

[22] Filed: May 23, 1994

Related U.S. Application Data

[63] Continuation of Ser. No. 982,581, Nov. 27, 1992, abandoned.

[30] Foreign Application Priority Data

Nov. 29, 1991 [JP] Japan .................................. 3-316874

[51] Int. Cl.$^6$ .............................. C12N 9/48; C12N 9/50; C12N 9/64
[52] U.S. Cl. ........................... 435/212; 435/219; 435/226
[58] Field of Search .................................... 435/212, 219, 435/226

OTHER PUBLICATIONS

Ohwaki et al. (1993) *Atherosclerosis*, 102(2), 227–228.
Ohnaka et al. (1993) *J. Biol. Chem.*, 268(35), 26759–26766.
Ikura et al. (1994) *Biochem. Biophys. Res. Comm.*, 203(3), 1417–1422.
Okada et al. (1990) *Biochem. Biophys. Res. Comm.*, 171(3), 1192–1198.
Sawamura et al. (1990) *Biochem. Biophys. Res. Comm.*, 172(2), 883–889.
Sawamura et al. (1993) *Biochim. Biophys. Acta*, 1161, 295–302.
Sakai et al. (19 Oct. 1993) JP 05,268,956 in *Chem. Abst.*, 120 395, Abst #72,415.
Sakai et al. (31 Jul. 1992) JP 04,210,593 in *Chem Abst.*, 117, Abst #229,115.
Knap et al. (1993) *J. Cardiovasc. Pharmacol.*, 22(Suppl. 8), 590–593, in *Chem. Abst.*, 120(17), 549, Abst #73,979.
Shinmi et al. (1993) *J. Cardiovas. Pharmacol.* 22(Suppl. 8), 561–564, in *Chem Abst* 120(17), 394–395, Abst #211,159.
Wilkinson et al. (1993) *Biochem. Soc. Trans.*, 21(3), 276 S.
Takeda et al, *Biochemical and Biophysical Research Communications*, vol. 176, pp. 860–865 (1991).
Hioki et al, *Biochemical and Biophysical Research Communications*, vol. 174, pp. 446–451 (1991).
Okada et al, *Biochemical and Biophysical Research Communications*, vol. 171, pp. 1192–1198 (1990).
Marselle et al, *FASEB JOURNAL*, vol. 5, p. A1417 (1991) Abstract.
Matsumura et al, *FEBS*, vol. 272, pp. 166–169 (1990).
Sakai et al, *Chemical Abstracts*, vol. 117, (1992) abstract No. 229115y.
Ahn et al, *Proc. Natl. Acad. Sci. USA*, vol. 89, pp. 8606–8610 (1992).
Opgenorth et al, *FASEB Journal*, vol. 6, pp. 2653–2659 (1992).
Ohnaka et al. (1990) *Biochem. Biophys. Res. Comm.*, 168(3), 1128–1136.

Ikegawa et al. (1990A) *Biochem. Biophys. Res. Comm.*, 167(2), 860–866.
Ikegawa et al. (1990B) *Biochem. Biophys. Res. Comm.*, 171(2), 669–675.
Takada et al. (1991) *Biochem. Biophys. Res. Comm.*, 176(2), 860–865.
Takada et al. (1992) *Biochem. Biophys. Res. Comm.*, 182(3), 1383–1388.
Sawamura et al. (1990) *Biochem. Biophys. Res. Comm.*, 169(3), 1138–1144.
Sawamura et al. (1991) *Biochem. Biophys. Res. Comm.*, 174(2), 779–784.
Okada et al. (1990) *Biochem. Biophys. Res. Comm.*, 171(3), 1192–1198.
Okada et al. (1991) *Biochem. Biophys. Res. Comm.*, 180(2), 1019–1023.
Matsumura et al. (1990) *FEBS Lett*, 272(½), 166–170.
Matsumura et al. (1992) *Life Sci.*, 51, 1603–1611.
Ohwaki et al. (1993) *FEBS Lett*, 320(2), 165–168.
Batley et al. (1993) *FASEB J.*, 7(3), A330, Meeting Abst #1912.
Opgenorth (1992) *FASEB J.*, 6(9), 2653–2659.
Ahn et al. (1992) *Proc. Nat. Acad. Sci., USA*, 89(18), 8606–8610.
Hioki et al. (1991) *Biochem. Biophys. Res. Comm.*, 174(2), 446–451.
Takaoka et al. (1990) *Biochem. Biophys. Res. Comm.*, 173(3), 1218–1223.
WuWong et al. (1990) *Biochem. Biophys. Res. Comm.*, 171(3), 1291–1296.
Télémaque et al. (1991) *Nauyn–Schmiedeberg Arch. Pharmacol.*, 344, 505–507.
Rubanyi et al. (1991) *FASEB J.*, 5 2713–2720.
Hashim et al. (1991) *Life Sci.* 49(24), PL 207–PL 211.
McMahon et al. (1991) *Proc. Nat. Acad. Sci., USA*, 88(3), 703–707.
Devine et al. (1991) *FASEB J.*, 5(5), A1417, Abst #6072.
Sawamura et al. (1993) *Biochim Biophys. Acta*, 1161(2–3), 295–302, in *Chem Abs*, 118 427, Abst #186465.
Wu–Wong et al. (1991) *J. Cardiovas. Pharmacol.* 17(Suppl. 7), 520–525, in *Chem Abst.*, 116(9), Abst #79016.

(List continued on next page.)

Primary Examiner—David M. Naff
Assistant Examiner—Jon P. Weber
Attorney, Agent, or Firm—Oblon, Spivak, McClelland, Maier & Neustadt

[57] ABSTRACT

Human endothelin converting enzyme (ECE) has been isolated from blood or placenta by a series of centrifugation steps at different densities. A first ECE-I is isolated by a low speed centrifugation to produce enzyme with a hydrated density of about 0.94 g/ml. A second high speed centrifugation produces an ECE-II with a hydrated density between about 0.94 to about 1.006 g/ml. After adjusting the density of the solution, a high speed centrifugation isolates an ECE-III with a hydrated density between about 1.006 to about 1.063. A final adjustment to the density of the solution and high speed centrifugation obtains an ECE-IV with a hydrated density of between about 1.063 to about 1.210 g/ml.

5 Claims, 5 Drawing Sheets

OTHER PUBLICATIONS

Yano et al. (1991) *J. Cardiovas. Pharmacol., 17(Suppl. 7), 526–528,* in *Chem Abst.,* 116(9), Abst #79017.

Galvani et al. (1991) *J. Cardiovas. Pharmacol.,* 17 (Suppl. 7), 547–551, in *Chem. Abst.,* 116(9), Abst #79018.

Conversion of Big Endothelin–1 Membrane–Bound Metalloendopeptidase in Cultured Bovine Endothelial Cells Kenji Okada, et al. Biochemistry, Central Research Laboratories, Banyo Pharmaceutical co., Ltd. 2–9–3 Shimomeguro, Meguro–ku, Tokyo 153, Japan vol. 171, No1 3, 1990 Sep. 28, 1990 pp. 1192–1198.

Purification and Characterization of Putative Endothelin Converting Enzyme in Bovine Adrenal Medulla:Evidence for a Cathepsin D–Like Enzyme Tatsuya Sawamura, et al. Department of Biochemistry and #Department of Pharmacology, Institute of Basic Medical Sciences, University of Tsukuba, Tsukuba, Ibaraki 305, Japan vol. 168 No. 3, 1990 May 18, 1990 pp. 1230–1237.

A Novel Potent Vasoconstrictor Peptide Produced by Vascular Endothelial Cells Masashi Yanagisawa, et al. Institute of Basic Medical Sciences, University of Tsukuba, Tsukuba, Ibaraki 305, Japan Fermentation Research Institute, Agency of Industrial Science and Technology, Tsukuba, Ibaraki 305, Japan Third Department of Internal Medicine, University of Tokyo, Hongyo, Tokyo 113, Japan Nature vol. 332 Mar. 31, 1988 pp. 411–415.

I : FRACTION RANGE OF ENDOTHELIN CONVERTING ENZYME I
II : FRACTION RANGE OF ENDOTHELIN CONVERTING ENZYME II
III : FRACTION RANGE OF ENDOTHELIN CONVERTING ENZYME III
IV : FRACTION RANGE OF ENDOTHELIN CONVERTING ENZYME IV

HUMAN ENDOTHELIN CONVERTING ENZYME ISOLATED FROM BLOOD OR PLACENTA BY HYDRATED DENSITY

This application is a continuation of application Ser. No. 07/982,581, filed on Nov. 27, 1992, now abandoned.

BACKGROUND OF THE INVENTION

This invention relates to endothelin converting enzymes of mammalian cell origin or mammalian blood origin having the activity of converting big endothelin to endothelin, and a process for preparing the enzymes from mammal cells or mammal blood by extraction and purification.

Endothelin is an endothelial cell-derived vasocontrictor peptide discovered by Yanagisawa et al. in 1988, the presence of which has been identified in porcine, bovine and human [M. Yanagisawa et al., Nature, Vol. 332, 411 (1988)].

Endothelin includes 3 isopeptides named endothelin-1, endothelin-2 and endothelin-3, respectively. Of these isopeptides, endothelin-1 has been confirmed to show the highest activity in human body. Endothelin possesses strong and lasting action of constricting vascular smooth muscle cell and trachea, and induces hypertension and constriction of respiratory tract and, at a high concentration (i.e., about 1–about 50 pmol/ml in blood level), it can additionally induces ischemic cerebral and cardiac diseases such as cerebral apoplexy, stenocardia, myocardial infarction, cardiac incompetence and arrhythmia, nephropathy such as nephritis, circulatory failure of lung, liver and intestine, and asthma, thus in some cases killing animals.

Endothelin-1 is a 21-amino acid peptide which is produced by hydrolytically cleaving its precursor peptide, big endothelin-1 of the formula:

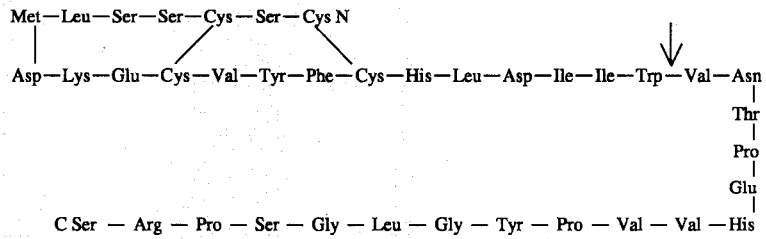

with the endothelin converting enzyme at the bond between the tryptophane residue at the 21st position from the Nterminus and the valine residue at the 22nd position from the N-terminus (shown by the downward arrow). This hydrolysis process is considered to be essential for production of endothelin-1 in vivo. Reports on enzymes having the endothelin converting activity have been made on those in cultured bovine endothelial cells [K. Okada et al., Biochemical and Biophysical Research Communications, Vol. 171, No. 3, 1192 (1990)] and those in bovine adrenal medulla [T. Sawamura et al., Biochemical and Biophysical Research Communications, Vol. 168, No. 3, 1230 (1990)], but no reports have been made on enzymes of human origin having an endothelin converting activity.

Endothelin, which has remarkable physiological activities as described above, is produced enzymatically from its precursor, big endothelin and, therefore, serves to provide a means for inhibiting in vivo production of endothelin. In addition, this enzyme is expected to provide a useful reagent for analyzing the mechanism of vasoconstriction in vivo and for studying various diseases induced by endothelin.

Further, with elucidation of the endothelin converting enzyme, there can be provided an effective means for searching and developing an inhibitor of the enzyme, which is expected to be a means for prophylaxis and treatment of various diseases (hyperendothelinemia) induced by hypersecretion of endothelin, such as hypertension, constriction of trachea, ischemic brain diseases and heart diseases, nephropathy, circulation failure of various organs (e.g., lung, intestine, etc.), and asthma.

For the above-described reasons, there has been desired the elucidation of endothelin converting enzyme of human origin not having so far been found and a process for obtaining it.

SUMMARY OF THE INVENTION

As a result of intensive investigations to obtain endothelin converting enzymes of human origin, we have found that enzymes having an endothelin converting activity exist in a lipoprotein fraction of human cells and blood. Further investigations have led to the discovery that those enzymes exist in the lipoprotein fraction of mammalian cells and blood.

It is an object of the present invention to provide endothelin converting enzymes of mammalian cell origin or mammalian blood origin, having the activity of converting big endothelin to endothelin and further having a hydrated density of up to about 0.94 g/ml, about 0.94 g/ml–about 1.006 g/ml, about 1.006 g/ml–about 1. 063 g/ml or about 1.063 g/ml–about 1.210 g/ml.

Another object of the present invention is to provide a process for preparing the endothelin converting enzymes from mammalian cell or blood by centrifugation process or/and gel filtration process.

Other objects, features and advantages of the present invention will become apparent from the detailed description of the preferred embodiments of the invention to follow.

DETAILED DESCRIPTION OF THE INVENTION

Figure 1:
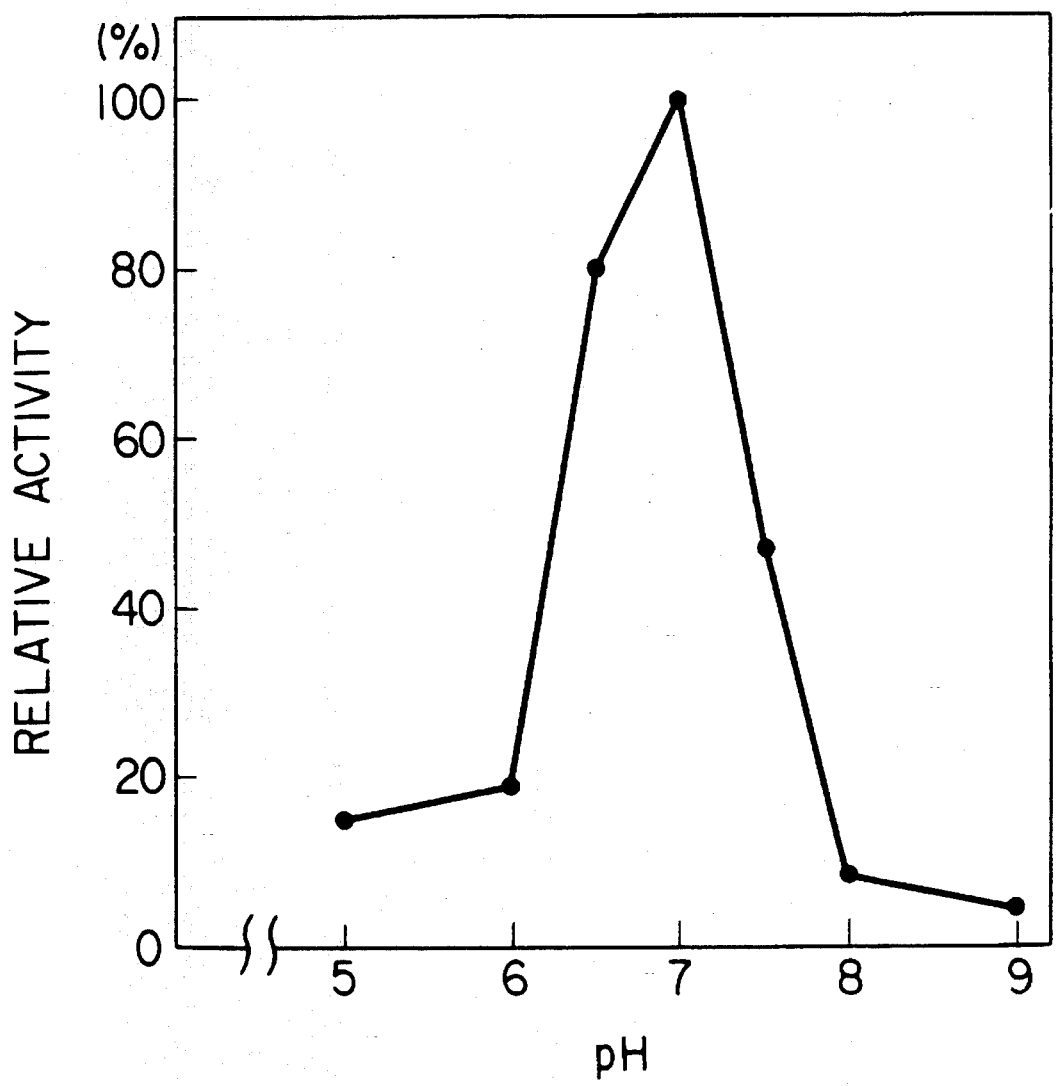
FIG. 1 is a graph showing the test results at optimum pH for endothelin converting enzyme I obtained in Example 1.
Figure 2:
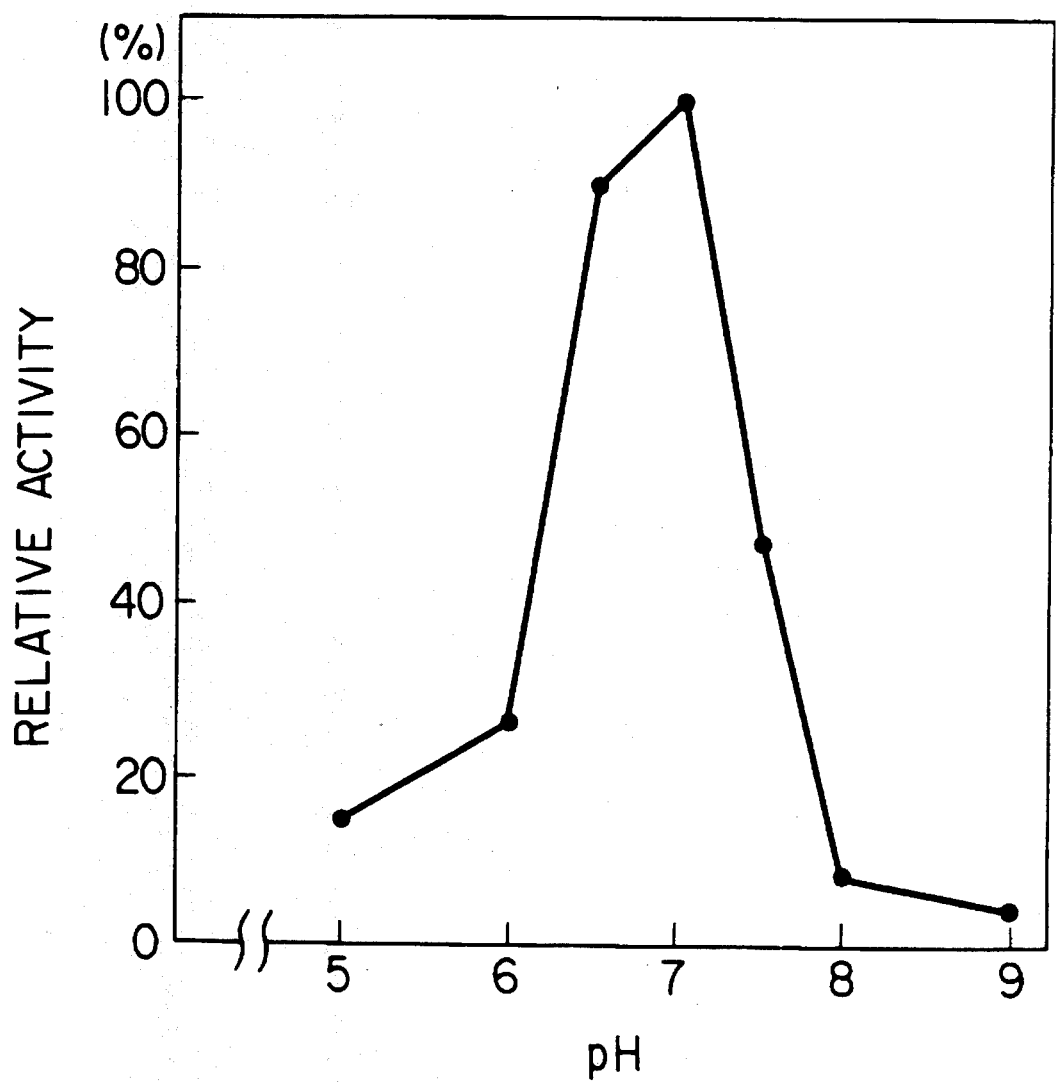
FIG. 2 is a graph showing the test results at optimum pH for endothelin converting enzyme II obtained in Example 2.
Figure 3:
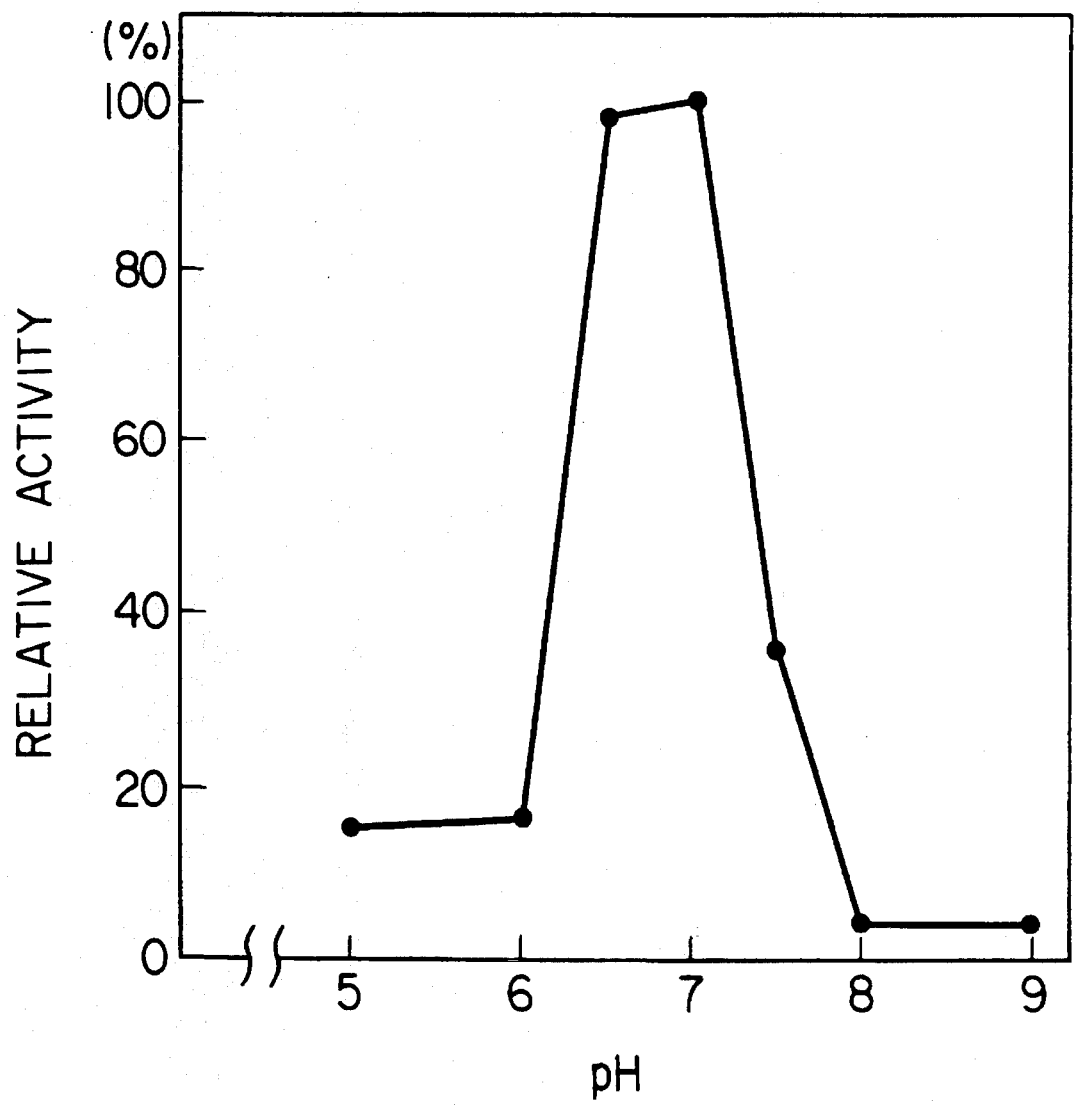
FIG. 3 is a graph showing the test results at optimum pH for endothelin converting enzyme III obtained in Example 3.
Figure 4:
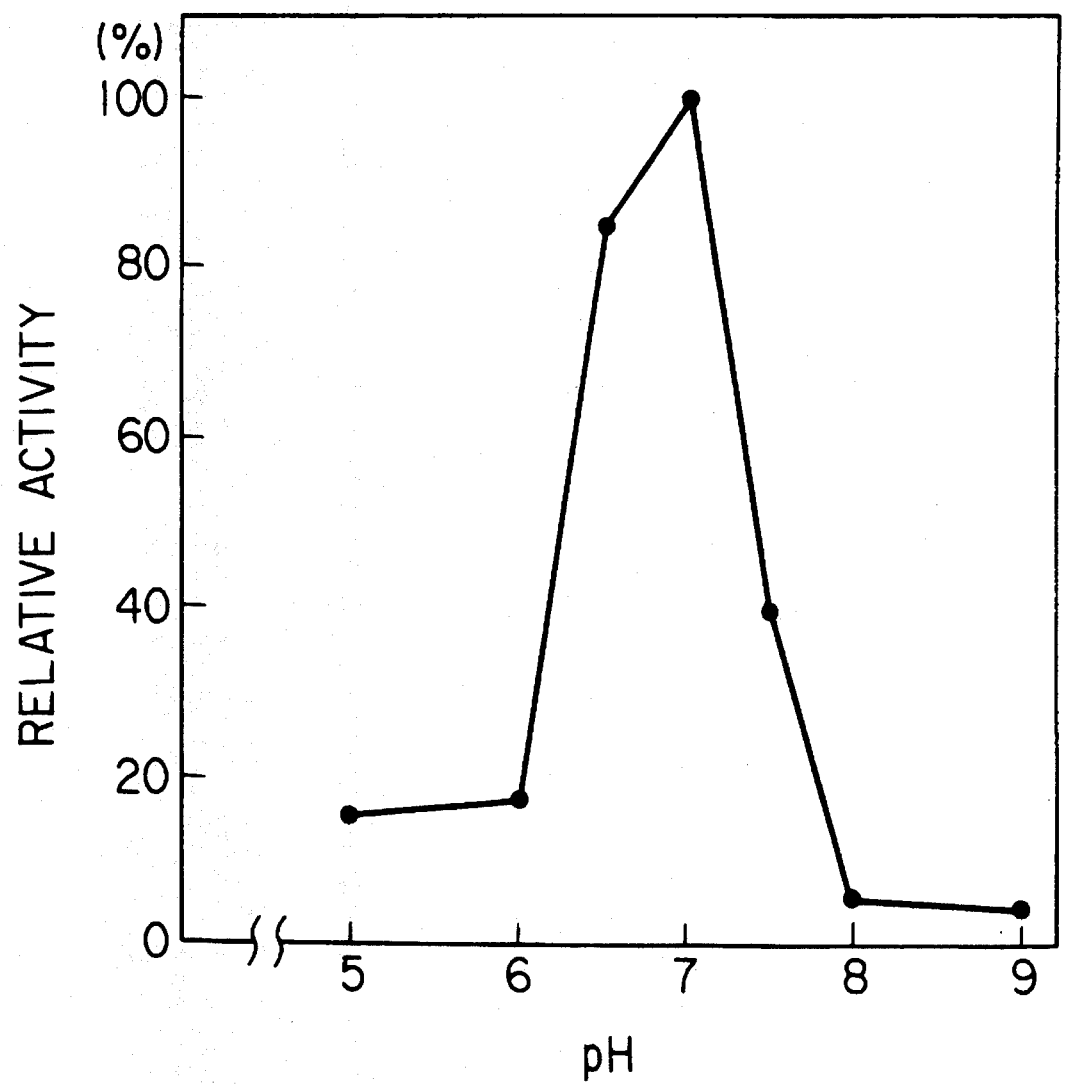
FIG. 4 is a graph showing the test results at optimum pH for endothelin converting enzyme IV obtained in Example 4.
Figure 5:
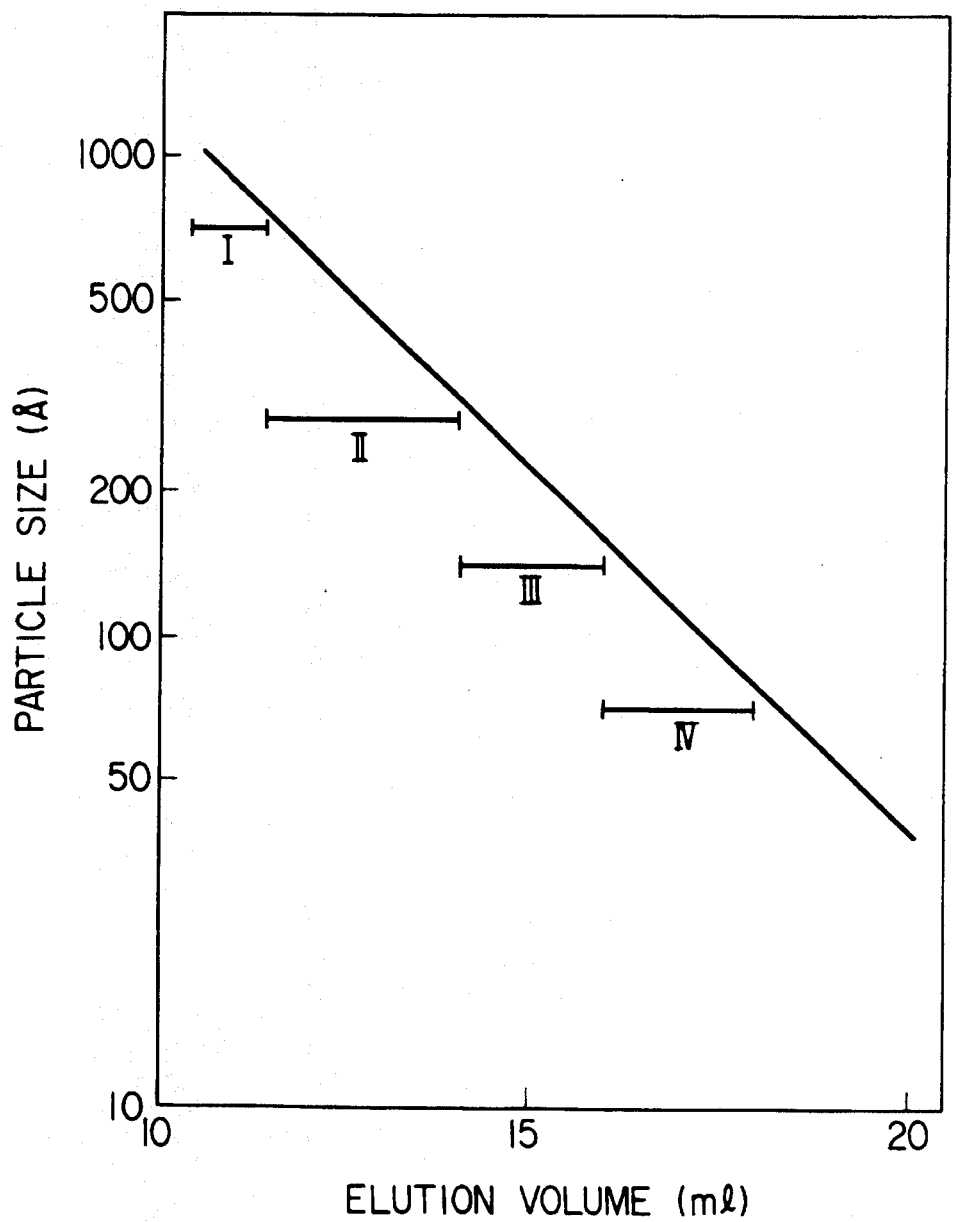
FIG. 5 is a graph showing a standard curve for measuring particle size by gel filtration process using TSK-G5000PW and the test results for determing particle sizes of endothelin converting enzymes I, II, III and IV obtained in Examples 1, 2, 3 and 4, respectively.

The endothelin converting enzymes of the present invention are obtained from cells of human or other mammalian organs or tissues such as liver, small intestine, placenta, blood endothelium, kidney and cerebrum, cultured cells of the origin of these cells, or human or other mammalian blood by centrifuging process. When human organs or the like are used as the starting material of the enzyme, blood or placenta is advantageously used because of its availability. However, other organs or tissues than blood and placenta may also be used as the starting material with sacrificing availability.

The endothelin converting enzymes of the invention are of the origin of mammalian cells and blood, have the ability of converting big endothelin to endothelin, and have a hydrated density of up to about 0.94 g/ml, about 0.94 g/ml–about 1.006 g/ml, about 1.006 g/ml–about 1.063 g/ml or about 1.063 g/ml–about 1.210 g/ml.

The endothelin converting enzymes of the invention comprise endothelin converting enzyme I having a hydrated density of up to about 0.94 g/ml and being obtained by subjecting mammalian blood serum or plasma to centrifugation at 10,000 to 30,000 g for 10–30 minutes to obtain a fraction floating to the surface (fraction I) containing the enzyme I, endothelin converting enzyme II having a hydrated density of about 0.94 g/ml–about 1.006 g/ml and being obtained by subjecting the fraction I-free serum or plasma to centrifugation at 100,000 to 200,000 g for 16–24 hours to obtain a fraction floating to the surface (fraction II) containing the enzyme II, endothelin converting enzyme III having a hydrated density of about 1.006 g/ml–about 1.063 g/ml and being obtained by adding a salt to the fraction I-and fraction II-free serum or plasma to adjust the density to about 1.063 g/ml and subjecting it to centrifugation at 100,000 to 200,000 g for 16–24 hours to obtain a fraction floating to the surface (fraction III) containing the enzyme III, and endothelin converting enzyme IV having a hydrated density of about 1.063 g/ml–about 1.210 g/ml and being obtained by adding a salt to the fraction I-, fraction II-, and fraction III-free serum or plasma to adjust the density to about 1.210 g/ml and subjecting it to contrifugation at 100,000 to 200,000 g for 24–40 hours to obtain a fraction floating to the surface (fraction IV) containing the enzyme IV.

In another embodiment of the invention, the endothelin converting enzymes I, II, III and IV can be obtained by homogenizing mammalian organs or tissues or cultured cells of these organs or tissues, collecting a 10 supernatant of the resulting homogenate, adjusting the density of the supernatant to about 1.006 g/ml, and repeating the procedure of centrifugation and adjustment of density as with the blood serum or plasma.

In other embodiments of the invention, the endothelin converting enzymes II, III and IV can be obtained by removing endothelin converting enzyme I from mammalian blood serum or plasma by centrifugation, adjusting a density of the remaining serum or plasma to about 1.210 g/ml, centrifuging it, collecting a fraction floating to the surface, and subjecting the fraction to gel filtration column chromatography.

Alternatively, the endothelin converting enzymes II, III and IV can be obtained by homogenizing mammalian organs or tissues in a buffer, centrifuging the homogenate, adjusting density of a supernatant to about 1.006 g/ml, again centrifuging it to remove endothelin converting enzyme I, adjusting density of the supernatant to about 1.210 g/ml, centrifuging it, collecting a fraction floating to the surface, and subjecting the fraction to gel filtration column chromatography.

Of the thus-obtained four endothelin converting enzymes, endothelin converting enzyme I having a hydrated density of up to about 0.94 g/ml has the following properties.
(a) Action
  It can convert big endothelin to endothelin.
(b) Substrate specificity
  It acts on big endothelin-1 to yield endothelin-1. In addition, it acts on big endothelin-2 to yield endothelin-2. Further, it acts on big endothelin-3 to yield endothelin-3.
(c) Optimum pH: 6.5–7.5
(d) Hydrated density: up to about 0.94 g/ml
(e) Inhibitors: ethylenediaminetetraacetate (EDTA), 1,10-phenanthroline and phosphoramidon
(f) Particle size: 750 Å or more
(g) Electrophoretic mobility
  It scarcely moves from the starting point (Electrophoresis on paper).

Endothelin converting enzyme II having a hydrated density of about 0.94 g/ml–about 1.006 g/ml has the following properties.
(a) Action
  It can convert big endothelin to endothelin.
(b) Substrate specificity
  It acts on big endothelin-1 to yield endothelin-1. In addition, it acts on big endothelin-2 to yield endothelin-2. Further, it acts on big endothelin-3 to yield endothelin-3.
(c) Optimum pH: 6.5–7.5
(d) Hydrated density: about 0.94 g/ml–about 1.006 g/ml
(e) Inhibitors: ethylenediaminetetraacetate (EDTA), 1,10-phenanthroline and phosphoramidon
(f) Particle size: about 300–about 750 Å
(g) Electrophoretic mobility
  It moves to the position of $\alpha_2$ globulin (Electrophoresis on paper).

Endothelin converting enzyme III having a hydrated density of about 1.006 g/ml–about 1.063 g/ml has the following properties.
(a) Action
  It can convert big endothelin to endothelin.
(b) Substrate specificity
  It acts on big endothelin-1 to yield endothelin-1. In addition, it acts on big endothelin-2 to yield endothelin-2. Further, it acts on big endothelin-3 to yield endothelin-3.
(c) Optimum pH: 6.5–7.5
(d) Hydrated density: about 1.006 g/ml–about 1.063 g/ml
(e) Inhibitors: ethylenediamine tetraacetate (EDTA), 1,10-phenanthroline and phosphoramidon
(f) Particle size: about 160–about 300 Å
(g) Electrophoretic mobility
  It moves to the position of $\beta$ globulin (Electrophoresis on paper).

Endothelin converting enzyme IV having a hydrated density of about 1.063 g/ml–about 1.210 g/ml has the following properties.
(a) Action
  It can convert big endothelin to endothelin.
(b) Substrate specificity
  It acts on big endothelin-1 to yield endothelin-1. In addition, it acts on big endothelin-2 to yield endothelin-2. Further, it acts on big endothelin-3 to yield endothelin-3.

(c) Optimum pH: 6.5–7.5
(d) Hydrated density: about 1.063 g/ml–about 1.210 g/ml
(e) Inhibitors: ethylenediaminetetraacetate (EDTA), 1,10-phenanthroline and phosphoramidon
(f) Particle size: about 80–about 160 Å
(g) Electrophoretic mobility It moves to the position of $\alpha_1$ globulin (Electrophoresis on paper).

The endothelin converting enzymes I–IV of the invention are obtained from mammalian organs or tissues such as liver, small intestine, placenta, vascular endothelium, kidney and cerebrum, cells obtained by cultured cells of these organs or tissues, or mammalian blood.

For example, in the case of using blood as a starting material, the enzymes are obtained in the following manner. That is, blood serum or plasma is first separated from blood, and the serum or plasma is subjected to centrifugation (centrifugation procedure I) at 4°–25° C., preferably 4°–15° C., for 10–30 minutes at 10,000 g–30,000 g. After the centrifugation procedure, a fraction floating to the surface (fraction I) is collected to obtain endothelin converting enzyme I of the present invention. Then, the fraction I-free sample is subjected to contrifugation at 4°–25° C., preferably 4°–15° C., for 16–24 hours at 100,000 g–200,000 g (centrifugation procedure II), and a fraction floating to the surface (fraction II) is collected to obtain endothelin converting enzyme II. Subsequently, the fraction II-free sample is adjusted to about 1.063 g/ml in density by adding thereto a salt such as potassium bromide and to about 7.0 in pH, subjected to centrifugation at 4°–25° C., preferably 4°–15° C., for 16–24 hours at 100,000 g–200,000 g (centrifugation procedure III), and a fraction floating to the surface (fraction III) is collected to obtain endothelin converting enzyme III. Subsequently, the fraction III-free sample is adjusted to about 1.210 g/ml in density by adding thereto a salt such as potassium bromide and to about 7.0 in pH, subjected to centrifugation at 4°–25° C., preferably 4°–15° C., for 24–40 hours at 100,000 g–200,000 g (centrifugation procedure IV), and a fraction floating to the surface (fraction IV) is collected to obtain endothelin converting enzyme IV.

Alternatively, in the case of using organs and tissues as starting materials, the enzymes can be obtained in the following manner. That is, organs or tissues are cut into fine pieces, a suitable amount of buffer such as a 25 mM HEPES-0.25M sucrose buffer (pH 7.4) is added thereto, and the mixture is homogenized in a commonly employed homogenizer such as a Potter-Elvehjem homogenizer at a low temperature. The thus obtained homogenate is then subjected to centrifugation to collect a supernatant. The supernatant obtained by the above-described procedure is further centrifuged at 50,000 g–100,000 g to obtain another supernatant which is a fraction of cytosol of the organs or tissues. This cytosolic fraction is dialyzed against a sodium chloride aqueous solution adjusted to about 1.006 g/ml in density or is subjected to a desalting column equilibrated with a sodium chloride aqueous solution, followed by elution with the same sodium chloride aqueous solution, to thereby replacing the solvent of the cytosolic fraction with the sodium chloride aqueous solution of about 1.006 g/ml in density. This cytosolic fraction is repeatedly subjected to the centrifugation procedure and adjustment of density as is the same with blood serum or plasma to obtain endothelin converting enzymes I, II, III and IV of the invention.

Activity of the endothelin converting enzyme of the invention is expressed in terms of activity of converting big endothelin-1 to endothelin-1, which is measured in the following manner. (1) Method for measuring enzyme activity 10 μl of a 100 nmol/ml big endothelin-1 solution is added to 1 ml of an enzyme solution (10 mM trishydrochloric acid–0.15M sodium chloride buffer; pH 7.0), and the enzymatic reaction is carried out at 37° C. for 3 hours. After completion of the reaction, 10 μl of a 0.1M EDTA solution is added thereto to discontinue the reaction. Thereafter, the resultant endothelin-1 is assayed according to the sandwich-EIA method. An enzymatic activity of converting 1 pmol of big endothelin-1 to endothelin-1 per hour under the above-described reaction conditions is termed 1 U (unit).

(2) Sandwich-EIA method

A sample and a predetermined concentration of endothelin standard solution are respectively applied to a 96-hole microplate on which ani-endothelin monoclonal antibody is immobilized to thereby cause the enzymatic reaction. After completion of the reaction, the wells are washed. Then, biotin-labeled anti-endothelin polyclonal antibody and peroxydase-labeled avidin are applied thereto for reaction. After washing the microplate, activity of bound peroxydase is assayed. Endothelin concentration in the sample is assayed based on the calibration curve drawn by using endothelin standard solutions having predetermined concentrations of endothelin.

(3) Preparation of anti-endothelin monoclonal antibody

A mouse is immuned with a conjugate between endothelin-1 and Keyhole limpet hemocyanin, and splenocytes of the immuned mouse and mouse myeloma are fused in a conventional manner to prepare a hybridoma, followed by cloning the hybridoma capable of yielding an antibody for endothelin-1. Monoclonal antibody yielded by the cloned hybridoma is purified by a Protein A column to prepare anti-endothelin-1 monoclonal antibody.

(4) Anti-endothelin-1 polyclonal antibody

A rabbit is immuned with a conjugate between endothelin-1 and Keyhole limpet hemocyanin of Cellana mazatlandica to obtain antiserum. An antibody fraction is obtained from the antiserum using a protein A column. The antibody fraction is applied to a column on which big endothelin-1 is immobilized, and a fraction bound to the column is collected to prepare anti-endothelin-1 polyclonal antibody. The resulting anti-endothelin-1 polyclonal antibody is bound to biotin to prepare a biotin-labelled anti-endothelin polyclonal antibody.

Enzymatic and chemical properties of the endothelin converting enzymes I–IV of the present invention will be described below.

(a) Substrate specificity

10 μl of a 100 nmol/ml of big endothelin-1 or big endothelin-2 or big endothelin-3 solution is added to 1 ml of the endothelin converting enzyme I, II, III or IV of the invention, and the enzymatic reaction is carried out at 37° C. for 3 hours. After completion of the reaction, 10 μl of a 0.1M EDTA solution is added thereto to discontinue the reaction. Then, production of endothelin-1 or endothelin-2 or endothelin-3 is examined according to the sandwich-EIA method specific to endothelin-1, endothelin-2 or endothelin-3. As a result, it is found that the endothelin converting enzymes I, II, III and IV of the present invention produce endothelin-1 from big endothelin-1, endothelin-2 from big endothelin-2 and endothelin-3 from big endothelin-3.

(b) Optimum pH

Optimum pH of the endothelin converting enzyme of the invention is measured by adding the endothelin converting enzyme to a solution of big endothelin in 50 mM buffer with varying pH level, and conducting the reaction at 37° C. Buffer solutions used are as follows.

pH 3.5–6.0 Acetic acid-sodium acetate buffer pH 6.0–7.0 PIPES-sodium hydroxide buffer
pH 7.0–9.0 Tris-hydrochloric acid buffer
pH 9.0–12.0 Sodium carbonate-sodium hydroxide buffer Measurement of the optimum pH has revealed that the endothelin converting enzymes I–IV of the present invention exhibit the highest activity in a range of pH 6.5–7.5.

(c) Hydrated density

Hydrated density of the endothelin converting enzymes I–IV measured according to the ultracentrifugation method has revealed that endothelin converting enzyme I has a hydrated density of up to about 0.94 g/ml, endothelin converting enzyme II about 0.94 g/ml to about 1.006 g/ml, endothelin converting enzyme III about 1.006 g/ml to about 1.063 g/ml and endothelin converting enzyme IV about 1.063 g/ml to about 1.210 g/ml.

(d) Inhibitors

The enzymes of the invention were tested for the effects of various inhibitors against the activity of converting big endothelin-1 to endothelin-1.

Each of the enzymes is incubated in 100 μl of a reaction solution (10 mM tris-hydrochloric acid-0.15M sodium chloride buffer; pH 7.0) containing various inhibitors at 37° C. for 30 minutes, and the residual enzymatic activity is measured in the above-described manner. Residual activities in the presence of various inhibitors are tabulated below taking the activity of untreated enzyme as 100.

Table 1 shows the results with endothelin converting enzyme I, Table 2 with endothelin converting enzyme II, Table 3 with endothelin converting enzyme III and Table 4 with endothelin converting enzyme IV.

TABLE 1

| Inhibitor | Concentration (mM) | Relative Activity (%) |
|---|---|---|
| Control | — | 100 |
| Ethylenediaminetetraacetate (EDTA) | 1 | 2 |
| 1,10-Phenanthroline | 0.5 | 10 |
| Phosphoramidon | 0.1 | 1 |
| Pepstatin A | 0.01 | 99 |

TABLE 2

| Inhibitor | Concentration (mM) | Relative Activity (%) |
|---|---|---|
| Control | — | 100 |
| Ethylenediaminetetraacetate (EDTA) | 1 | 7 |
| 1,10-Phenanthroline | 0.5 | 5 |
| Phosphoramidon | 0.1 | 2 |
| Pepstatin A | 0.01 | 100 |

TABLE 3

| Inhibitor | Concentration (mM) | Relative Activity (%) |
|---|---|---|
| Control | — | 100 |
| Ethylenediaminetetraacetate (EDTA) | 1 | 10 |
| 1,10-Phenanthroline | 0.5 | 7 |
| Phosphoramidon | 0.1 | 1 |
| Pepstatin A | 0.01 | 99 |

TABLE 4

| Inhibitor | Concentration (mM) | Relative Activity (%) |
|---|---|---|
| Control | — | 100 |
| Ethylenediaminetetraacetate (EDTA) | 1 | 5 |
| 1,10-Phenanthroline | 0.5 | 8 |
| Phosphoramidon | 0.1 | 3 |
| Pepstatin A | 0.01 | 97 |

(e) Particle size

Particle sizes of the endothelin converting enzymes I, II, III and IV are measured to be more than about 750 Å, about 300–about 750 Å, about 160–about 300 Å and about 80–about 160 Å, respectively, by gel filtration column chromatography using a column of TSK-G5000PW® (Tosoh K.K.) to thereby separate together with a spheric protein whose Stoke's radius is known.

(f) Electrophoretic mobility

As a result of electrophoresis (using a barbital buffer of pH 8.6) on a filter paper (No. 1, Whatman Co.) at a constant voltage of 110 V for 16 hours, it has been found that the endothelin converting enzyme I scarecely moves from the starting point, that the endothelin converting enzyme II moves to the $\alpha_2$ globulin position, that the endothelin converting enzyme III moves to the $\beta$ globulin position, and that the endothelin converting enzyme IV moves to the $\alpha_1$ globulin position.

(g) Confirmation that the endothelin converting activity of the lipoprotein fraction is provided by the lipoprotein itself Human serum is adjusted to about 1.210 g/ml in density by adding thereto potassium bromide, then centrifuged for 20 hours at 100,000 g. A fraction floating to the surface is collected to obtain a fraction (fraction A) containing all of the endothelin converting enzymes I, II, III and IV. To this fraction A are added dextran sulfate and manganese chloride so as to provide final concentrations of 0.65% and 0.2M, respectively, followed by allowing to stand at room temperature for 2 hours to precipitate lipoprotein contained in the fraction A. The lipoprotein precipitate is removed by centrifugation at 4° C. for 30 minutes at 20,000 g to obtain a lipoprotein-free fraction (fraction B). Measurement of the endothelin converting activity of the fraction B in the above-described manner has revealed that endothelin converting activity of the fraction B is up to 5% of that of the fraction A. Thus, it was confirmed that the endothelin converting activity of the lipoprotein-containing fraction is provided by the lipoprotein itself.

The invention is further illustrated by the following examples.

EXAMPLE 1

Preparation of endothelin converting enzyme I from human blood 20 ml of human blood was coagulated to obtain 8 ml of blood serum. This serum was placed in a centrifuge tube Beckmann Co.; Ultraclear® tube; 14×89 mm), and a solvent of 1.006 g/ml in density (0.196M sodium chloride solution) was overlayered. The tube was centrifuged in a rotor, SW41Ti (Beckmann Co.) at 25,000 g for one hour (centrifugation procedure I). After centrifugation, 4 ml of an upper layer was collected by separation, again placed in a centrifuge tube (Beckmann Co.; Ultraclear® tube; 14×89 mm), and a solvent of about 1.006 g/ml in density (0.196M sodium chloride aqueous solution) was overlayered. The tube was centrifuged in the same manner as described above at 15° C. for one hour at 25,000 g (centrifugation procedure II). 4 ml of an upper layer was collected by separation to obtain endothelin converting enzyme I. Additionally, the resultant endothelin converting enzyme I had an activity of 20 U.

EXAMPLE 2

Preparation of endothelin converting enzyme II from human blood

A solvent of about 1.006 g/ml (0.196M sodium chloride aqueous solution) was overlayered 8 ml of the lower layer in the centrifugation procedure I of Example 1, subjected to centrifugation at 15° C. and 120,000 g for 18 hours (centrifugation procedure III), and 2 ml of the upper layer was collected by separation. This layer was then subjected to column chromatography using a NAP-10® column (Pharmacia Co.) equilibrated with a 10 mM tris-hydrochloric acid-0.15M sodium chloride buffer (pH 7.0), the same buffer being used as an eluent. Thus, there was obtained endothelin converting enzyme II having the activity of 90 U.

EXAMPLE 3

Preparation of endothelin converting enzyme III from human blood 0.822 g of potassium bromide was added to 10 ml of the lower layer in the centrifugation procedure III of Example 2 to dissolve. To this solution was added about 3 ml of a solvent of about 1.063 g/ml (prepared by adding 0.822 g of potassium bromide to 10 ml of a 0.196M sodium chloride aqueous solution), followed by mixing to prepare a uniform solution. After adjusting pH of the solution to about 7.0, the solution was subjected to centrifugation (centrifugation procedure IV) at 15° C. and 120,000 g for 20 hours in a rotor of SW41Ti (Beckmann Co.), and 2 ml of an upper layer was collected by separation. This layer was then subjected to column chromatography using a NAP-10® column (Pharmacia Co.) equilibrated with a 10 mM tris-hydrochloric acid-0.15M sodium chloride buffer (pH 7.0 ), the same buffer being used as an eluent. Thus, there was obtained endothelin converting enzyme III having the activity of 70 U.

EXAMPLE 4

Preparation of endothelin converting enzyme IV from human blood 2.32 g of potassium bromide was added to 10 ml of the lower layer in the centrifugation procedure IV of Example 3 to dissolve. To this solution was added about 3 ml of a solvent of about 1.210 g/ml (prepared by adding 3.31 g of potassium bromide to 10 ml of a 0.196M sodium chloride aqueous solution), followed by mixing to prepare a uniform solution. After adjusting pH of the solution to about 7.0, the solution was subjected to centrifugation (centrifugation procedure V) at 15° C. and 120,000 g for 40 hours in a rotor of SW41Ti (Beckmann Co.), and 2 ml of an upper layer was collected by separation. This layer was then subjected to column chromatography using a NAP-10® column (Pharmacia Co.) equilibrated with a 10 mM tris-hydrochloric acid-0.15M sodium chloride buffer (pH 7.0), the same buffer being used as an eluent. Thus, there was obtained endothelin converting enzyme IV having the activity of 20 U.

EXAMPLE 5

Preparation of endothelin converting enzyme I from porcine blood

Endothelin converting enzyme I was obtained from porcine blood in the same manner as described in Example 1.

EXAMPLE 6

Preparation of endothelin converting enzyme II from porcine blood

Endothelin converting enzyme II was obtained from porcine blood in the same manner as described in Example 2.

EXAMPLE 7

Preparation of endothelin converting enzyme III from porcine blood

Endothelin converting enzyme III was obtained from porcine blood in the same manner as described in Example 3.

EXAMPLE 8

Preparation of endothelin converting enzyme IV from porcine blood

Endothelin converting enzyme IV was obtained from porcine blood in the same manner as described in Example 4.

EXAMPLE 9

Preparation of human placenta cytosolic fraction

Human placenta (about 5 g) was freed of membrane, well washed with physiological saline, and cut into fine pieces. 20 ml of a 25 mM HEPES-0.25M sucrose buffer (pH 7.4) was added to the placenta pieces, followed by homogenizing the mixture in a Potter-Elvehjem homogenizer. The resultant homogenate was centrifuged at 1,000 g for 20 minutes, and a supernatant was collected by separation. This supernatant was again centrifuged at 10,000 g for 20 minutes, and another supernatant was collected by separation. The resultant supernatant was centrifuged at 100,000 g for 2 hours. Thus, about 20 ml of a supernatant was recovered as a cytosolic fraction.

EXAMPLE 10

Preparation of endothelin converting enzyme I from human placenta

The human placenta cytosolic fraction obtained in Example 9 was subjected to column chromatography using a column of PD-10® (Pharmacia Co.) equilibrated with a 0.196M saline with the same solvent being eluent. 8 ml of the eluate was placed in a centrifuge tube (Beckmann Co.; Ultraclear® tube; 14×89 mm), and a solvent of about 1.006 g/ml in density (0.196M sodium chloride solution) was overlayered. The tube was subjected to centrifugation (centrifugation procedure I) at 15° C. and 25,000 g for one hour using a rotor of model SW41Ti (Beckmann Co. ). After the centrifugation, 4 ml of an upper layer was collected by separation, again placed in a centrifuge tube (Beckmann Co.; Ultraclear® tube; 14×89 mm), and a solvent of about 1.006 g/ml in density (0.196M sodium chloride aqueous solution) was overlayered. The tube was subjected to centrifugation (centrifugation procedure II) in the same manner as described above at 15° C. and 25,000 g for one hour. After the centrifugation, 4 ml of an upper layer was collected by separation to obtain endothelin converting enzyme I having an activity of 25 U.

EXAMPLE 11

Preparation of endothelin converting enzyme II from human placenta

A solvent of about 1.006 g/ml in density (0.196M sodium chloride solution) was overlayered 8 ml of the lower layer obtained in the centrifugation procedure I of Example 10. The tube containing it was subjected to centrifugation (centrifugation procedure III) at 15° C. and 120,000 g for 18 hours using a rotor of model SW41Ti (Beckmann Co.). After the centrifugation, 2 ml of an upper layer was collected by separation, subjected to column chromatography using a column of NAP-10 (Pharmacia Co.) equilibrated with a 10 mM tris-hydrochloric acid-0.15M sodium chloride buffer (pH 7.0) with the same buffer being used as an eluent to obtain endothelin converting enzyme II having an activity of 150 U.

EXAMPLE 12

Preparation of endothelin converting enzyme III from human placenta 0.822 g of potassium bromide was added to 10 ml of the lower layer in the centrifugation procedure III of Example 11 to dissolve. To this solution was added about 3 ml of a solvent of about 1.063 g/ml in density (prepared by adding 0.822 g of potassium bromide to 10 ml of a 0.196M sodium chloride aqueous solution), followed by mixing to prepare a uniform solution. After adjusting pH of the solution to about 7.0, the solution was subjected to centrifugation (centrifugation procedure IV) at 15° C. and 120,000 g for 20 hours in a rotor of SW41Ti (Beckmann Co.), and 2 ml of an upper layer was collected by separation. This layer was then subjected to column chromatography using a NAP-10® column (Pharmacia Co.) equilibrated with a 10 mM tris-hydrochloric acid-0.15M sodium chloride buffer (pH 7.0), the same buffer being used as an eluent. Thus, there was obtained endothelin converting enzyme III having the activity of 150 U.

EXAMPLE 13

Preparation of endothelin converting enzyme IV from human placenta 2.32 g of potassium bromide was added to 10 ml of the lower layer in the centrifugation procedure IV of Example 12 to dissolve. To this solution was added about 3 ml of a solvent having a density of about 1.210 g/ml (prepared by adding 3.31 g of potassium bromide to 10 ml of a 0.196M sodium chloride aqueous solution), followed by mixing to prepare a uniform solution. After adjusting pH of the solution to about 7.0, the solution was subjected to centrifugation (centrifugation procedure V) at 15° C. and 120,000 g for 40 hours in a rotor of SW41Ti (Beckmann Co.), and 2 ml of an upper layer was collected by separation. This layer was then subjected to column chromatography using a NAP-10® column (Pharmacia Co.) equilibrated with a 10 mM tris-hydrochloric acid-0.15M sodium chloride buffer (pH 7.0), the same buffer being used as an eluent. Thus, there was obtained endothelin converting enzyme IV having the activity of 25 U.

EXAMPLE 14

Preparation of endothelin converting enzymes II, III and IV from human blood by gel filtration method 2.65 g of potassium bromide was added to 8 ml of the lower layer in centrifugation procedure I of Example 1 to dissolve. After adjusting pH of the solution to about 7.0, six about 1.25 ml portions of the solution (7.5 ml total) were placed in 6 centrifuge tubes (3PC tubes, Hitachi Co., Ltd.), respectively, and about 1.25 ml of a solvent of about 1.210 g/ml in density (prepared by adding 3.31 g of potassium bromide to 10 ml of a 0.196M sodium chloride aqueous solution) was overlayered each of the six solutions. The tubes were subjected to centrifugation at 15° C. and 100,000 g for 20 hours using a rotor of model RP100AT4 (Hitachi Co., Ltd.), 0.75 ml of an upper layer in each centrifuge tube was collected by separation, placed in a dialysis tube ( molecular weight cut off 50,000; Spectrum Co.) and dialyzed for one day and one night against a 10 mM tris-hydrochloric acid-0.15M sodium chloride buffer (pH 7.0) to obtain 6 ml of a mixture of endothelin converting enzymes II, III and IV. After completion of the dialysis, the mixture of endothelin converting enzymes II, III and IV was concentrated to about 300 µl by placing the dialysis tube retaining it in powdery Sephadex® G75 (Pharmacia Co.). 50 µl of the thus-concentrated mixture of endothelin converting enzymes II, III and IV was chromatographed over a column of TSK-G4000SW® (7.5 mmφ×60 cm; Tosoh K.K.) equilibrated with a 10 mM tris-hydrochloric acid-0.15M sodium chloride buffer (pH 7.0) using the same buffer as an eluent. Fractions corresponding to elution volumes of 10 ml–11.5 ml (fraction I), 11.5 ml–16.75 ml (fraction II) and 16.75 ml–20.75 ml ( fraction III) were collected, and endothelin converting enzymes II, III and IV were obtained from the fractions I, II and III, respectively.

EXAMPLE 15

Preparation of endothelin converting enzymes II, III and IV from human placenta by gel filtration method The human placenta cytosolic fraction obtained in Example 9 was chromatographed over a column of PD-10® (Pharmacia Co.) equilibrated with a 0.196M saline using the same solvent, as an eluent. 2.65 g of potassium bromide was added to 8 ml of this eluate to dissolve. After adjusting pH of the solution to about 7.0, six about 1.25 ml portions of the solution (7.5 ml total) were placed in 6 centrifuge tubes (3PC tubes, Hitachi Co., Ltd.), respectively, and about 1.25 ml of a solvent of about 1.210 g/ml in density (prepared by adding 3.31 g of potassium bromide to 10 ml of a 0.196M sodium chloride aqueous solution) was overlayered each of the six solutions. The tubes were subjected to centrifugation at 15° C. and 100,000 g for 20 hours using a rotor of model RP100AT4 (Hitachi Co., Ltd.), 0.75 ml of an upper layer in each centrifuge tube was collected by separation, placed in a dialysis tube (molecular weight cut off 50,000; Spectrum Co.) and dialyzed for one day and one night against a 10 mM tris-hydrochloric acid-0.15M sodium chloride buffer (pH 7.0) to obtain 6 ml of a mixture of endothelin converting enzymes II, III and IV. After completion of the dialysis, the mixture of endothelin converting enzymes II, III and IV was concentrated to about 300 µl by placing the dialysis tube retaining it in powder Sephadex® G75 (Pharmacia Co.). 50 µl of the thus-concentrated mixture of endothelin converting enzymes II, III. and IV was chromatographed over a column of TSK-G4000SW® (7.5 mm φ×60 cm; Tosoh K.K.) equilibrated with a 10 mM tris-hydrochloric acid-0.15 M sodium chloride buffer (pH 7.0) using the same buffer as an eluent. Fractions corresponding to elution volumes of 10 ml–11.5 ml (fraction I), 11.5 ml–16.75 ml (fraction II) and 16.75 ml–20.75 ml (fraction III) were collected, and endothelin converting enzymes II, III and IV were obtained from the fractions I, II and III, respectively.

EXAMPLE 16

Confirmation that the endothelin converting activity of the lipoprotein fraction is provided by lipoprotein itself 20 ml of human blood was coagulated to obtain 8 ml of blood serum. 2.65 g of potassium bromide was added to 8 ml of the blood serum to dissolve. After adjusting pH of the solution to about 7.0, six about 1.25 ml portions of the solution (7.5 ml total) were placed in 6 centrifuge tubes (3PC tubes, Hitachi Co., Ltd.), respectively, and about 1.25 ml of a solvent of about 1.210 g/ml in density (prepared by adding 3.31 g of potassium bromide to 10 ml of a 0.196M sodium chloride aqueous solution) was overlayered each of the six solutions. The tubes were subjected to centrifugation at 15° C. and 100,000 g for 20 hours using a rotor of model RP100AT4 (Hitachi Co., Ltd.). 0.75 ml of an upper layer in each centrifuge tube was collected by separation, placed in a dialysis tube (molecular weight cut off 50,000; Spectrum Co.) and dialyzed for one day and one night against a 10 mM tris-hydrochloric acid-0.15M sodium chloride buffer (pH 7.0) to obtain a fraction containing all of endothelin converting enzymes I, II, III and IV (fraction A). Then, four 0.5 ml portions of fraction A were placed in four centrifuge tubes I–IV (3PC tubes, Hitachi Co., Ltd.), respectively. Further, 132.5 µl of a 10 mM tris-hydrochloric acid-0.15M sodium chloride buffer (pH 7.0) was added to centrifuge tube I, 32.5 µl of a 10% dextran sulfate aqueous solution and 100 µl of a 10 mM tris-hydrochloric acid-0.15M sodium chloride buffer (pH 7.0) to centrifuge tube II, 100 µl of 1M manganese chloride aqueous solution and 32.5 µl of a 10 mM tris-hydrochloric acid-0.15M sodium chloride buffer (pH 7.0) to centrifuge tube III, and 32.5 µl of 10% dextran sulfate aqueous solution and 100 µl of a 1M manganese chloride aqueous solution to centrifuge tube IV. After allowing to stand for 2 hours at room temperature, each of the centrifuge tubes I–IV was centrifuged at 4° C. and 20,000 g for 30 minutes using a rotor of model RP100AT (Hitachi Co., Ltd.). Supernatants were collected by separation from respective tubes. Thus, supernatant I was obtained from centrifuge tube I, supernatant II from centrifuge tube II, supernatant III from centrifuge tube III, and supernatant IV from centrifuge tube IV. Measurement of the endothelin converting activities of the supernatants I–IV revealed that the supernatants II, III and IV showed the activities of 105%, 110% and 4.4%, respectively, taking the activity of the supernatant I as 100%.

What is claimed is:

1. An isolated endothelin converting enzyme having an activity of converting big endothelin to endothelin, wherein said enzyme is isolated from human or porcine blood by the steps of:
   (i) separating serum or plasma from said blood;
   (ii) centrifuging said serum or plasma at 4° to 25° C. for 10–30 minutes at 10,000 to 30,000 g;
   (iii) removing a fraction I which floats to the surface;
   (iv) centrifuging the fraction I-free sample at 4°–25° C. for 16 to 24 hours at 100,000 to 200,000 g;
   (v) removing a fraction II which floats to the surface;
   (vi) adjusting the density of the remaining sample, which is free of fraction II to about 1.063 g/ml and the pH to about 7.0;
   (vii) centrifuging the sample of (vi) at 4°–25° C. for 16–24 hours at 100,00 to 200,000 g; and
   (viii) collecting a fraction III which floats to the surface and contains endothelin converting enzyme which has a hydrated density of about 1.006 to about 1.063 g/ml.

2. An isolated endothelin converting enzyme obtained according to claim 1, which further comprises the steps of:
   (ix) adjusting the density of the remaining sample, which is free of fraction III, to about 1.210 g/ml and the pH to about 7;
   (x) centrifuging the sample of (ix) at 4°–25° C. for 24 to 40 hours at 100,000 to 200,000 g;
   (xi) collecting a fraction IV which floats to the surface and contains an endothelin converting enzyme which has a hydrated density of about 1.063 to about 1.210 g/ml.

3. The isolated endothelin converting enzyme of claim 1 wherein said enzyme is isolated from human blood.

4. An isolated endothelin converting enzyme, having an activity of converting big endothelin to endothelin, wherein said enzyme is isolated from human placenta by the steps of:
   (a) homogenizing the tissue or organ in a buffer;
   (b) centrifuging the homogenate and collecting a supernatant;
   (c) centrifuging the supernatant at 50,000 to 100,000 g and collecting a second supernatant;
   (d) replacing the solvent of said second supernatant with an aqueous salt solution of about 1.006 g/ml density;
   (e) centrifuging the solution obtained in (d) at 4° to 25° C. for 10–30 minutes at 10,000 to 30,000 g;
   (f) removing a fraction I which floats to the surface;
   (g) centrifuging the fraction I-free sample at 4°–25° C. for 16 to 24 hours at 100,000 to 200,000 g;
   (h) removing a fraction II which floats to the surface;
   (i) adjusting the density of the remaining sample, which is free of fraction II, to about 1.063 g/ml and the pH to about 7.0;
   (j) centrifuging the sample of (vi) at 4°–25° C. for 16–24 hours at 100,00 to 200,000 g; and
   (k) collecting a fraction III which floats to the surface and contains endothelin converting enzyme which has a hydrated density of about 1.006 g/ml to about 1.063 g/ml.

5. An isolated endothelin converting enzyme isolated according to claim 4, which further comprises the steps of:
   (l) adjusting the density of the remaining sample, which is free of fraction III, to about 1.210 g/ml and the pH to about 7;
   (m) centrifuging the sample of (ix) at 4°–25° C. for 24 to 40 hours at 100,000 to 200,000 g;
   (n) collecting a fraction IV which floats to the surface and contains an endothelin converting enzyme which has a hydrated density of about 1.063 to about 1.210 g/ml.

* * * * *

UNITED STATES PATENT AND TRADEMARK OFFICE
CERTIFICATE OF CORRECTION

PATENT NO. : 5,462,869
DATED : OCTOBER 31, 1995
INVENTOR(S) : TATSUYA OHWAKI ET AL

It is certified that error appears in the above-indentified patent and that said Letters Patent is hereby corrected as shown below:

Column 13: line 56, "100,00" should read --100,000--;

Column 14: line 39, "100,00" should read --100,000--.

Signed and Sealed this

Sixth Day of August, 1996

Attest:

BRUCE LEHMAN

Attesting Officer

Commissioner of Patents and Trademarks